United States Patent
Kim

(10) Patent No.: US 9,218,459 B2
(45) Date of Patent: Dec. 22, 2015

(54) INTEGRATED DRUG MANAGEMENT SYSTEM AND METHOD OF PROVIDING PRESCRIPTION DRUGS BY USING THE SAME

(75) Inventor: Jun-Ho Kim, Daegu (KR)

(73) Assignee: JVM CO., LTD., Daegu (KR)

(*) Notice: Subject to any disclaimer, the term of this patent is extended or adjusted under 35 U.S.C. 154(b) by 381 days.

(21) Appl. No.: 13/460,824

(22) Filed: Apr. 30, 2012

(65) Prior Publication Data
US 2012/0284041 A1 Nov. 8, 2012

(30) Foreign Application Priority Data
May 3, 2011 (KR) .................. 10-2011-0042006

(51) Int. Cl.
G06Q 50/22 (2012.01)
G06F 19/00 (2011.01)

(52) U.S. Cl.
CPC .................. *G06F 19/3462* (2013.01)

(58) Field of Classification Search
None
See application file for complete search history.

(56) References Cited

U.S. PATENT DOCUMENTS

| 7,792,349 | B2* | 9/2010 | Van Den Brink | 382/141 |
| 2003/0176942 | A1* | 9/2003 | Sleep et al. | 700/213 |
| 2007/0214014 | A1* | 9/2007 | Suwalski et al. | 705/3 |
| 2010/0228562 | A1* | 9/2010 | Luciano, Jr. et al. | 705/2 |
| 2012/0330684 | A1* | 12/2012 | Jacobs et al. | 705/3 |

FOREIGN PATENT DOCUMENTS

| DE | 20 2009 012 784 U1 | 3/2011 |
| EP | 0 803 440 A1 | 10/1997 |
| WO | 02/25568 A2 | 3/2002 |
| WO | 2005/017814 A1 | 2/2005 |
| WO | 2009/035329 A2 | 3/2009 |
| WO | 2010/002853 A2 | 1/2010 |

* cited by examiner

*Primary Examiner* — Michael Tomaszewski
(74) *Attorney, Agent, or Firm* — Novick, Kim & Lee, PLLC; Jae Youn Kim

(57) ABSTRACT

Disclosed are an integrated drug management system and a method of providing prescription drugs by using the same. The integrated drug management system includes a drug information managing module to manage a basic information and a pattern information of an individual drug by performing an image processing scheme for the individual drug, an integrated management control module to control a drug management work and a prescription drug management work, a prescription drug making module to provide the drug by preparing a drug according to a prescription information, a prescription drug inspecting module to inspect a defect state of the drug, a prescription drug reinspecting module connected to the integrated management control module to reinspect the defect state of the drug which has been determined as a defective drug, and a drug pack providing module to provide a drug pack to each ward or each patient.

25 Claims, 24 Drawing Sheets

INTEGRATED DRUG MANAGEMENT SYSTEM AND METHOD OF PROVIDING PRESCRIPTION DRUGS BY USING THE SAME

BACKGROUND OF THE INVENTION

1. Field of the Invention

The present invention relates to an integrated drug management system and a method of providing a prescription drug by using the same, in which a plurality of individual drugs can be managed by using pattern information based on images, and the defect of a prescription drug can be determined by comparing prescription information of the prescription drug with pattern information of the prescription drug.

2. Description of the Related Art

Recently, as various kinds of drugs are mass-produced, systems for integratedly managing drug information have been required in a large-scale pharmacy and a pharmacy belonging to a hospital to manage many kinds of drugs.

However, codes for managing the drugs may vary depending on hospitals, pharmacies or countries employing the drugs, and a standard to search for the drugs is not properly provided. Accordingly, the effective management of drug information may be difficult.

When handling individual drugs in order to make up a prescription, although the individual drugs have unique external appearance such as a color, a shape, a size, a thickness, and a symbol mark, there are many drugs having similar external appearance, so it may be difficult to distinguish the individual drugs from each other by naked eyes of a user or to search for the information of the individual drug.

In general, prescription drugs prepared in a hospital or a pharmacy are individually packaged in the unit of a dose and the packaged prescription drugs are provided to patients on the basis of the duration and frequency for taking the prescription drugs. Since the prescription drugs are sealed in an individual pack after the preparation of the prescription drugs has been finished, it is difficult to determine if the prescription drugs exactly match with prescription information.

In order to solve the above problem, a drug packing paper is made of a transparent material, so that drugs sealed by the packing paper can be easily recognized from the outside.

However, a hospital or a pharmacy, which manages a great amount of prescription drugs, requires great labor force and long inspection time in order to determine the normal preparation state of individually packaged drugs.

In addition, since errors caused due to drugs having the same color or size, or drugs having similar colors or sizes cannot be easily checked, the prescription drugs may be defective. The defective prescription drugs not only degrade the healing effect for patients, but cause fatal injury to the patients.

SUMMARY OF THE INVENTION

Accordingly, the present invention has been made keeping in mind the above problems occurring in the prior art, and an object of the present invention is to provide an integrated drug management system capable of managing information of an individual drug through an image processing scheme for the individual drug and integratedly managing drugs by determining the defect state of a prescription drug pack.

Another object of the present invention is to provide an integrated drug management system capable of managing the basic information of an individual drug pack and the pattern information of drugs by employing a drug information managing module.

Still another object of the present invention is to provide an integrated drug management system capable of analyzing an independent region of the image of an individual drug by employing a first image processing module.

Still another object of the present invention is to provide an integrated drug management system capable of calculating the pattern information of an individual drug image by employing a first drug pattern analyzing module.

Still another object of the present invention is to provide an integrated drug management system capable of preparing a drug according to prescription information and providing a prescription drug pack by employing a prescription drug making module.

Still another object of the present invention is to provide an integrated drug management system capable of analyzing an individual prescription drug pack and inspect a defect state of the individual prescription drug pack according to prescription information by employing a prescription drug inspecting module.

Still another object of the present invention is to provide an integrated drug management system capable of analyzing an independent region of each drug contained in an individual prescription drug pack by employing a second image processing module.

Still another object of the present invention is to provide an integrated drug management system capable of determining a defect state of the prescription drug pack based on the information of a drug pattern of the prescription drug pack by employing a second drug pattern analyzing module.

Still another object of the present invention is to provide an integrated drug management system capable of reinspecting the defect state of a prescription drug pack, which has been determined as a defective prescription drug pack, and correcting the prescription drug pack if the prescription drug pack is defective, by employing a prescription drug reinspecting module.

Still another object of the present invention is to provide an integrated drug management system capable of analyzing the independent region of each drug contained in the prescription drug pack, which has been determined as a defective prescription drug pack, by using a third image processing module.

Still another object of the present invention is to provide an integrated drug management system capable of determining a defect state of a prescription drug pack, which has been determined as a defective drug pack, based on the pattern information of each drug contained in the prescription drug pack by using a third drug pattern analyzing module.

Still another object of the present invention is to provide an integrated drug management system capable of providing prescription drug packs according to wards or patients by employing a drug pack providing module.

Still another object of the present invention is to provide a method of providing a prescription drug, capable of correcting a prescription drug pack, which has been determined as a defective pack, based on the pattern information of an individual drug, which has been previously registered, and providing a prescription drug exactly matching with prescription information.

Still another object of the present invention is to provide a method of providing a prescription drug, capable of computerizing a huge amount of individual drug information by creating and registering the pattern information of an individual drug.

Still another object of the present invention is to provide a method of providing a prescription drug, capable of photographing an individual drug at various angles and processing the image of the photographed individual drug.

Still another object of the present invention is to provide a method of providing a prescription drug, capable of creating the pattern information of an individual drug according to the appearance of the individual drug, by including a step of analyzing the pattern of the individual drug.

Still another object of the present invention is to provide a method of providing a prescription drug, capable of inputting the basic information of an individual drug and managing the basic information together with the pattern information of the individual drug.

Still another object of the present invention is to provide a method of providing a prescription drug, capable of automatically providing a prescription drug matching with prescription information, by including a step of preparing the prescription drug.

Still another object of the present invention is to provide a method of providing a prescription drug, capable of attaching an ID code containing prescription information to a prescription drug pack, thereby easily identifying the prescription drug pack and transferring information according to the preparation completion of the prescription drug in real time.

Still another object of the present invention is to provide a method of providing a prescription drug, capable of analyzing an individual drug contained in a prescription drug pack and determining the defect state of the prescription drug, by including a step of inspecting the defect of the prescription drug.

Still another object of the present invention is to provide a method of providing a prescription drug, capable of easily analyzing the prescription drug by easily photographing a prescription drug pack and analyzing the image of the photographed prescription drug pack.

Still another object of the present invention is to provide a method of providing a prescription drug, capable of analyzing the pattern of a prescription drug and comparing prescription information with the information of the prescription drug.

Still another object of the present invention is to provide a method of providing a prescription drug, capable of reinspecting the defect state of the defective prescription drug pack.

Still another object of the present invention is to provide a method of providing a prescription drug, capable of determining the defect of the prescription drug by comparing the defective prescription drug with the prescription information.

Still another object of the present invention is to provide a method of providing a prescription drug, capable of processing the image of prescription drugs contained in the defective prescription drug pack.

Still another object of the present invention is to provide a method of providing a prescription drug, capable of comparing the pattern information of the defective prescription drug with the prescription information by calculating the pattern information of the defective drug.

Still another object of the present invention is to provide a method of providing a prescription drug, capable of providing prescription drug packs according to wards or patients.

Still another object of the present invention is to provide a method of providing a prescription drug, capable of winding up and providing prescription drug packs and transmitting the provision information of the prescription drug packs to a hospital server.

In order to accomplish the above objects, according to one aspect of the present invention, there is provided an integrated drug management system including a drug information managing module to manage a basic information and a pattern information of an individual drug by performing an image processing scheme for the individual drug, an integrated management control module connected to the drug information managing module to control a drug management work and a prescription drug management work, a prescription drug making module connected to the integrated management control module to provide a prescription drug by preparing the prescription drug according to a prescription information, a prescription drug inspecting module connected to the integrated management control module to inspect a defect state of the prescription drug, a prescription drug reinspecting module connected to the integrated management control module to reinspect the defect state of the prescription drug which has been determined as a defective drug, and a drug pack providing module connected to the integrated management control module to provide a drug pack to each ward or each patient.

According to another aspect of the present invention, there is provided a method of providing a prescription drug. The method includes registering a pattern information of an individual drug by using a drug information managing module, preparing a drug based on a prescription information received from a hospital server by using a prescription drug making module, inspecting a defect state of the prescription drug by using a prescription drug inspecting module, and correcting the prescription drug determined as a defective drug by using a defective drug pack correcting module or a prescription drug making module.

As described above, according to the integrated drug management system of the present invention, the information of individual drugs are managed and the defect state of the prescription drug pack is determined through the image processing scheme for the individual drug, thereby integratedly managing a huge amount of drugs, improving the reliability of the prescription drug pack, and providing the safe prescription drug.

In addition, according to the integrated drug management system of the present invention, the basic information of an individual drug pack and the pattern information of drugs can be objectively and systematically managed by including the drug information managing module.

In addition, according to the integrated drug management system of the present invention, an independent region of the image of an individual drug can be analyzed by including the first image processing module.

Further, according to the integrated drug management system of the present invention, the pattern information of an individual drug image can be calculated and provided by including the first drug pattern analyzing module.

In addition, according to the integrated drug management system of the present invention, the prescription drug making module is included, thereby attaching or forming an ID code containing the information of drugs according to prescription information and the prescription information, automatically making a prescription drug, and rapidly providing the prescription drug pack.

Further, according to the integrated drug management system of the present invention, an individual prescription drug pack can be analyzed and a defect state of the individual prescription drug pack can be inspected according to prescription information by including the prescription drug inspecting module.

In addition, according to the integrated drug management system of the present invention, an independent region of each drug contained in the individual prescription drug pack can be analyzed and provided by including the second image processing module.

Further, according to the integrated drug management system of the present invention, a defect state of the prescription drug pack can be objectively determined based on the information of a drug pattern of the prescription drug pack by including the second drug pattern analyzing module.

In addition, according to the integrated drug management system of the present invention, the defect state of a prescription drug pack, which has been determined as a defective prescription drug pack, can be reinspected, and the prescription drug pack can be corrected if the prescription drug pack is defective, by including the prescription drug reinspecting module.

Besides, according to the integrated drug management system of the present invention, the independent region of each drug contained in the prescription drug pack, which has been determined as a defective pack, can be analyzed by including the third image processing module.

In addition, according to the integrated drug management system of the present invention, a defect state of a prescription drug pack, which has been determined as a defective drug pack, can be determined based on the pattern information of each drug contained in the prescription drug pack by including the third drug pattern analyzing module.

Further, according to the integrated drug management system of the present invention, the prescription drug pack providing module is included to provide the prescription drug packs according to wards or patients, so that the efficiency of supplying the prescription drug packs can be increased.

According to the method of providing the prescription drug of the present invention, a prescription drug pack, which has been determined as a defective pack, is corrected based on the pattern information of an individual drug, which has been previously registered, thereby providing a prescription drug exactly matching with prescription information.

According to the method of providing the prescription drug of the present invention, a huge amount of individual drug information can be systematically computerized by creating and registering the pattern information of an individual drug.

According to the method of providing the prescription drug of the present invention, an individual drug can be photographed at various angles and the image of the photographed individual drug can be automatically processed.

According to the method of providing the prescription drug of the present invention, the pattern information of an individual drug can be created and managed according to the appearance of the individual drug by including a step of analyzing the pattern of the individual drug.

According to the method of providing the prescription drug of the present invention, the basic information of an individual drug can be input and managed together with the pattern information of the individual drug.

According to the method of providing the prescription drug of the present invention, a prescription drug matching with prescription information can be automatically provided by including a step of preparing the prescription drug.

According to the method of providing the prescription drug of the present invention, an ID code containing prescription information can be attached to a prescription drug pack or can be formed in the prescription drug pack, thereby easily identifying the prescription drug pack and transferring information according to the preparation completion of the prescription drug in real time.

According to the method of providing the prescription drug of the present invention, an individual drug contained in a prescription drug pack can be analyzed and the defect state of the prescription drug can be determined by including a step of inspecting the defect of the prescription drug.

According to the method of providing the prescription drug of the present invention, the prescription drug can be easily analyzed by photographing a prescription drug pack and analyzing the image of the photographed prescription drug pack.

According to the method of providing the prescription drug of the present invention, the pattern of a prescription drug can be analyzed, thereby comparing prescription information with the information of the prescription drug.

According to the method of providing the prescription drug of the present invention, the reliability of the inspection for the defects of the prescription drug can be improved by reinspecting the defect state of the defective prescription drug pack.

According to the method of providing the prescription drug of the present invention, the defect of the prescription drug can be determined by comparing the defective prescription drug with the prescription information.

According to the method of providing the prescription drug of the present invention, the image of prescription drugs contained in the defective prescription drug pack can be processed.

According to the method of providing the prescription drug of the present invention, the pattern information of the defective prescription drug can be compared with the prescription information by calculating the pattern information of the defective prescription drug.

According to the method of providing the prescription drug of the present invention, prescription drug packs can be supplied according to wards or patients.

According to the method of providing the prescription drug of the present invention, prescription drug packs are wound up and provided, thereby transmitting the provision information of the prescription drug packs to a hospital server.

DETAILED DESCRIPTION OF THE INVENTION

Hereinafter, an integrated drug management system according to the present invention and a method of providing a prescription drug by using the same will be described in detail with reference to accompanying drawings.

Figure 1:
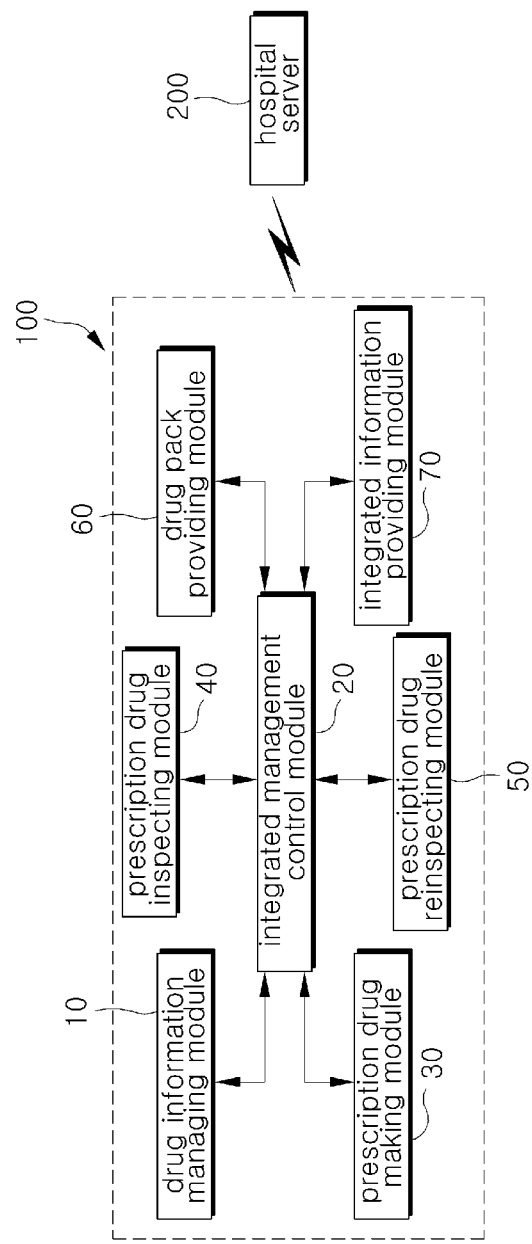
FIG. 1 is a block diagram showing the structure of an integrated drug management system according to the present invention.

FIG. 1 is a block diagram showing the whole structure of an integrated drug management system 100 according to the present invention. The integrated drug management system 100 according to the present invention includes a drug information managing module 10, an integrated management control module 20, a prescription drug making module 30, a prescription drug inspecting module 40, a prescription drug reinspecting module 50, a drug pack providing module 60, and an integrated information providing module 70.

Figure 2:
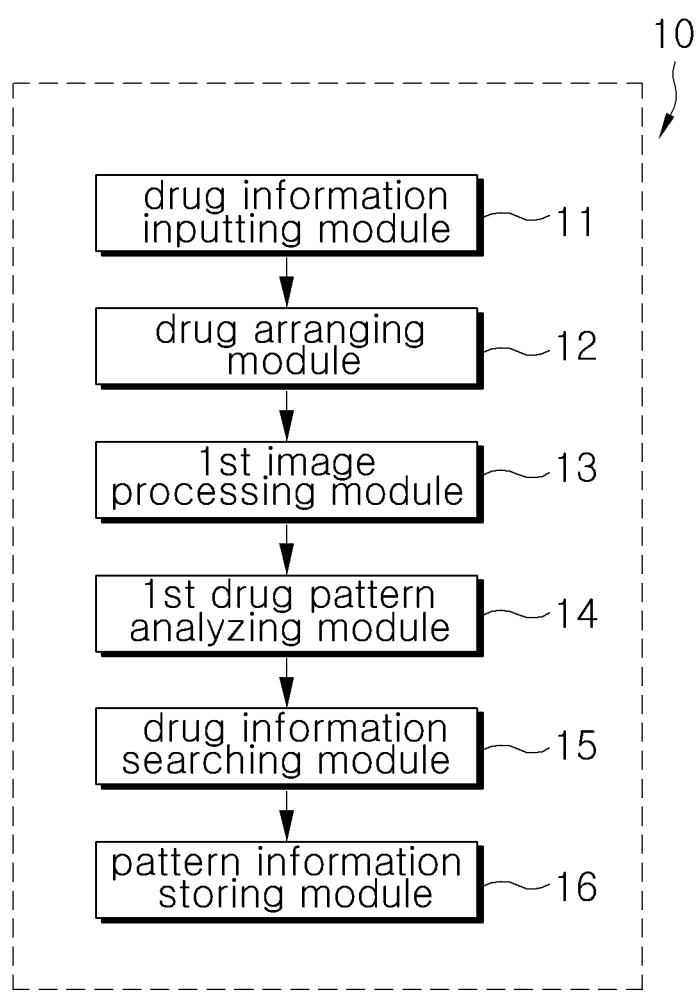
FIG. 2 is a block diagram showing the structure of a drug information managing module installed in the integrated drug management system according to the present invention.

The drug information managing module 10 manages the basic information and the pattern information of an individual drug. As shown in FIG. 2, the drug information managing module 10 includes a drug information inputting module 11, a drug arranging module 12, a first image processing module 13, a first drug pattern analyzing module 14, a drug information searching module 15, and a pattern information storing module 16.

The drug information inputting module 11 inputs the basic information of the individual drug to be registered, and the basic information of the individual drug according to the present invention preferably includes the name of the drug, the manufacturer of the drug, the expiration date of the drug, and the information of the manufacture date of the drug.

The drug arranging module 12 is connected to the drug information inputting module 11 to arrange the individual drug. The drug arranging module 12 according to the present invention is preferably equipped with a function of rotating the individual drug at various angles.

In addition, the information of the individual drug according to the present invention includes information of various patterns. Since information of patterns of the individual drug according to the rotation angles must be analyzed, the individual drug is preferably arranged after the individual drug has been rotated at various angles when the individual drug is arranged through the drug arranging module 12.

Figure 3:
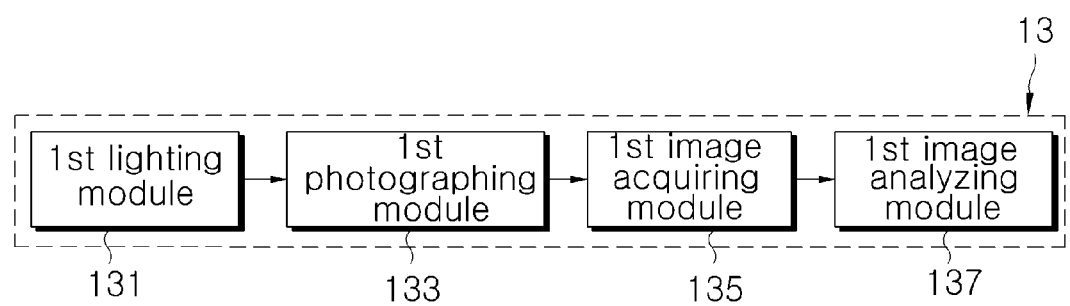
FIG. 3 is a block diagram showing the detailed structure of a first image processing module installed in the integrated drug management system according to the present invention.

The first image processing module 13 is connected to the drug arranging module 12 to photograph the individual drug and process the image of the individual drug. As shown in FIG. 3, the first image processing module 13 according to the present invention includes a first lighting module 131, a first photographing module 133, a first image acquiring module 135, and a first image analyzing module 137.

The first lighting module 131 illuminates the arranged individual drug. If the first lighting module 131 according to the present invention is adjusted, the color image and the black & white image of the individual drug can be obtained.

The first photographing module 133 is connected to the first lighting module 131 to photograph the arranged individual drug. The first image acquiring module 135 is connected to the first photographing module 133 to acquire an image frame of the individual drug.

The first image analyzing module 137 is connected to the first image acquiring module 135 to analyze the independent region of the image of the individual drug. The independent region of the individual drug is used to calculate the shape and the size of the individual drug according to the detection of the outer line of the individual drug.

Figure 4:
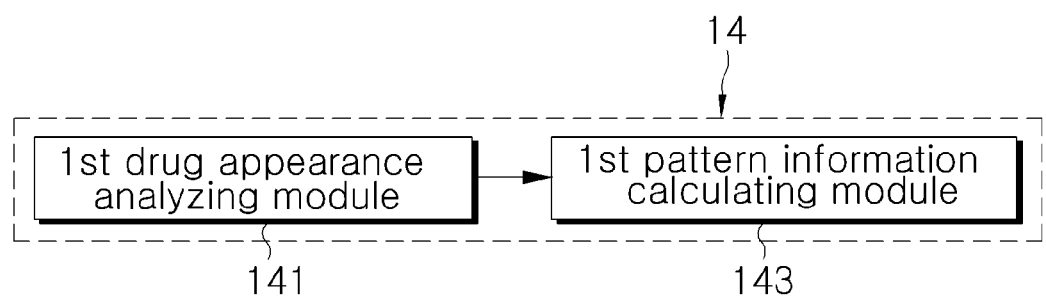
FIG. 4 is a block diagram showing the detailed structure of a first drug pattern analyzing module installed in the integrated drug management system according to the present invention.

The first drug pattern analyzing module 14 is connected to the first image processing module 13 to analyze the image of the individual drug so that the pattern of the individual drug can be analyzed. As shown in FIG. 4, the first drug pattern analyzing module 14 includes the first drug appearance analyzing module 141 and the first pattern information calculating module 143

The first drug appearance analyzing module 141 analyzes the information of the appearance of the individual drug by using the independent region of the image of the individual drug. The information of the appearance of the individual drug according to the present invention includes information of color, marking, a shape thickness, a length, a width, and an area.

The first pattern information calculating module 143 is connected to the first drug appearance analyzing module 141 to calculate pattern information containing an appearance graph and a shape code of the individual drug.

The appearance graph of the individual drug according to the present invention is calculated based on the distance from the center to the outer line of the individual drug. The shape code of the individual drug is calculated by classifying shape types according to the shape of the outer lines of the individual drug photographed at various angles.

The drug information searching module 15 is connected to the first drug pattern analyzing module 14 to search for the drug information which has been previously registered. The pattern information storing module 16 is connected to the drug information searching module 15 to store the basic information and the pattern information of the individual drug.

The integrated management control module 20 is connected to the drug information managing module 10 to manage the information of the individual information registered in the drug information managing module 10 and wholly control a work to inspect the defect state of the prescription drug.

Figure 5:
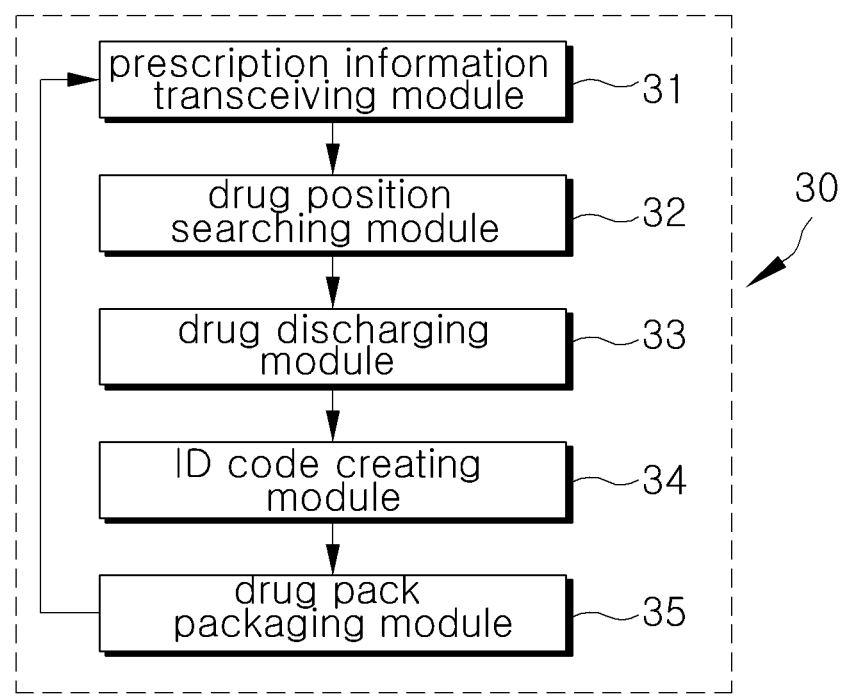
FIG. 5 is a block diagram showing the detailed structure of a prescription drug making module installed in the integrated drug management system according to the present invention.

The prescription drug making module 30 is connected to the integrated management control module 20 to make a prescription drug according to the prescription information and provide the prescription drug. The prescription drug making module 30 according to the present invention includes a prescription information transceiving module 31, a drug position searching module 32, a drug discharging module 33, a drug pack packaging module 35, and an ID code creating module 34 as shown in FIG. 5.

The prescription information transceiving module 31 transmits/receives prescription information to/from a prescription information server or a hospital server 200, and transfers information according to the preparation completion of the prescription drug to the integrated management control module 20.

The drug position searching module 32 is connected to the prescription information transceiving module 31 to search for the storage position of a drug corresponding to the prescription information. The drug discharging module 33 is connected to the drug position searching module 32 to discharge an individual drug matching with the prescription information.

The ID code creating module 34 is connected to the drug discharging module 33 to create an ID code containing the information of prescription drugs contained in a prescription drug pack, and to attach the created ID code to the prescription drug pack or to form the ID code in the prescription drug pack. The drug pack packaging module 35 is connected to the ID code creating module 34 to insert discharged prescription drugs into the prescription drug pack so that the prescription drugs can be packaged.

The ID code according to the embodiment of the present invention includes a bar code. The created bar code is printed on the prescription drug pack or attached to the prescription drug pack in the form of a sticker.

Figure 6:
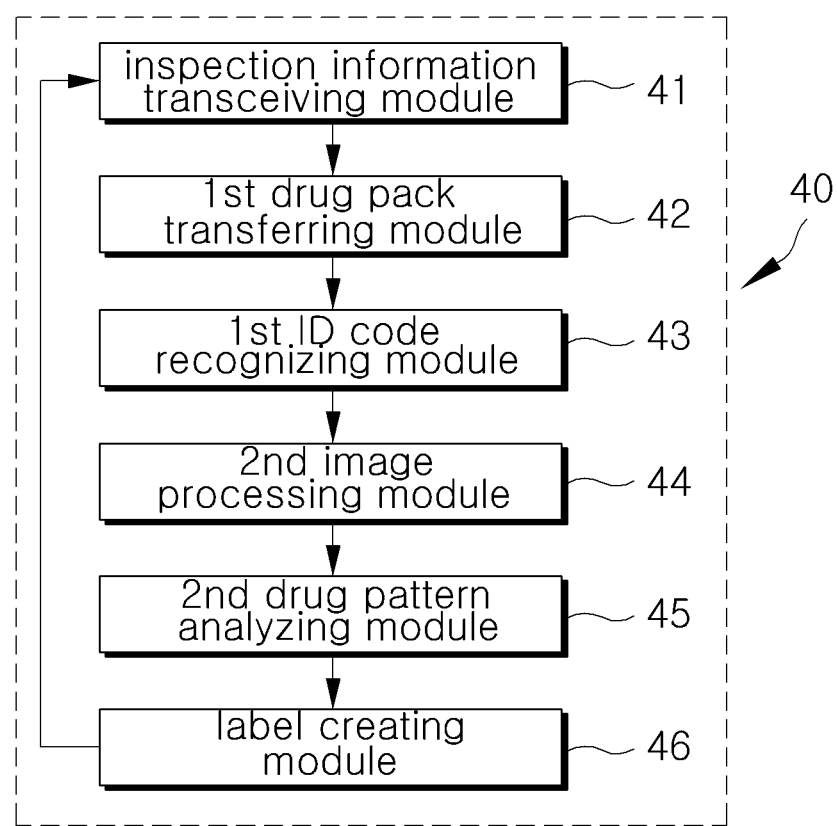
FIG. 6 is a block diagram showing the detailed structure of a prescription drug inspecting module installed in the integrated drug management system according to the present invention.

The prescription drug inspecting module 40 is connected to the integrated management control module to inspect the defect state of the prescription drugs. As shown in FIG. 6, the prescription drug inspecting module 40 includes an inspection information transceiving module 41, a first drug pack transferring module 42, a first ID code recognizing module 43, a second image processing module 44, a second drug pattern analyzing module 45, and a label creating module 46.

The inspection information transceiving module 41 receives the prescription information from the prescription information server or the hospital server 200, and transmits the inspection result of the prescription drug pack.

The first drug pack transferring module 42 is connected to the inspection information transceiving module 41 to sequentially transfer prescription drug packs. The first drug pack transferring module 42 according to the embodiment of the present invention includes a transfer belt to sequentially transfer a bundle of prescription drug packs on the transfer belt.

The first ID code recognizing module 43 is connected to the first drug pack transferring module 42 to recognize the ID code created by the ID code creating module 34.

The first ID code recognizing module 43 is provided to recognize the ID code formed on the prescription drug pack, so that the prescription information of the related prescription drug pack can be searched.

Figure 7:
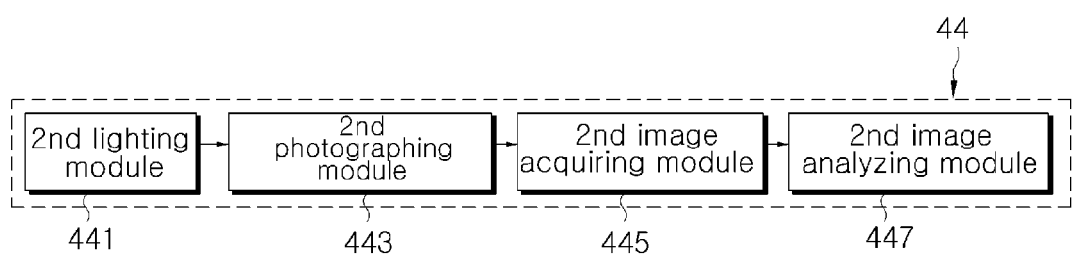
FIG. 7 is a block diagram showing the detailed structure of a second image processing module installed in the integrated drug management system according to the present invention.

The second image processing module 44 is connected to the first ID code recognizing module 43 to individually photograph the prescription drug pack so that the image of the prescription drug pack can be processed. As shown in FIG. 7, the second image processing module 44 includes a second lighting module 441, a second photographing module 443, a second image acquiring module 445, and a second image analyzing module 447.

The second lighting module 441 illuminates an individual prescription drug pack which is transferred by the first drug pack transferring module 42 and arranged, and the second photographing module 443 is connected to the second lighting module 441 to photograph the individual prescription drug pack.

The second photographing module 443 according to the present invention can acquire both of a color image and a black & white image of the prescription drug pack by adjusting the brightness of the second lighting module 441.

The second image acquiring module 445 is connected to the second photographing module 443 to acquire an image frame of the individual prescription drug pack. The second image analyzing module 447 is connected to the second image acquiring module 445 to analyze the independent region of an individual drug contained in the image of the individual prescription drug pack.

In addition, each image of the prescription drug pack having an image of an individual drug is acquired in photographing. The second image analyzing module 447 is provided to analyze the independent region of the individual drug contained in the prescription drug pack and extract the outer line of the individual drug.

Figure 8:
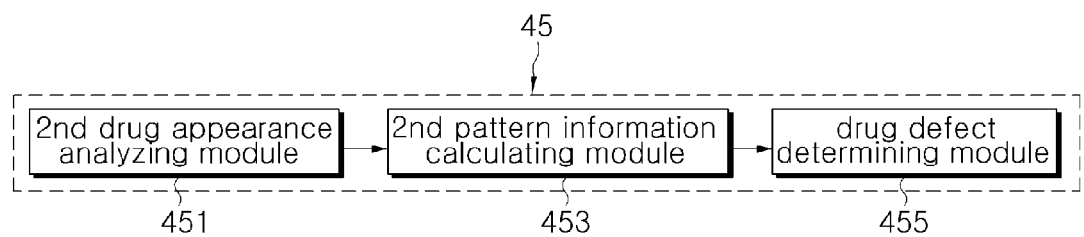
FIG. 8 is a block diagram showing the detailed structure of a second drug pattern analyzing module installed in the integrated drug management system according to the present invention.

The second drug pattern analyzing module 45 is connected to the second image processing module 44 to analyze the image of the prescription drug pack, analyze the pattern of the prescription drug, and determine the defect of the prescription drug. The second drug pattern analyzing module 45 according to the present invention includes a second drug appearance analyzing module 451, a second pattern information calculating module 453, and a drug defect determining module 455 as shown in FIG. 8.

The second drug appearance analyzing module 451 analyzes the appearance information of the individual drug by using the independent region of an individual drug image contained in an individual prescription drug pack image. The second pattern information calculating module 453 is connected to the second drug appearance analyzing module 451 to calculate the pattern information containing the appearance graph and the shape code of the individual drug.

The drug defect determining module 455 is connected to the second pattern information calculating module 453 to determine if the pattern information of the individual drug matches with drug information contained in the prescription information, thereby determining the defect state of the individual drug.

In other words, the pattern information of the individual drug calculated by analyzing a prescription drug image is compared with the pattern information of the individual drug stored in the drug information managing module 10 to determine if the calculated pattern information matches with the stored pattern information, so that the defect state of a prescription drug can be determined.

The label creating module 46 is connected to the second drug pattern analyzing module 45 to create a label representing the defect state of the prescription drug pack so that the label can be attached to the prescription drug pack. The label creating module 46 according to the present invention may attach the label only to a defective prescription drug pack or attach a label to distinguish a normal prescription drug pack from a defective prescription drug pack.

However, the defect state of the prescription drug pack cannot be exactly determined by performing only the defect inspection of the prescription drug inspecting module 40. This is because the pattern information of the individual drug may be erroneously calculated or cannot be calculated if individual drugs contained in the prescription drug pack are adjacent to each other or overlapped with each other when the prescription drug pack is photographed, so that the normal prescription drug pack may be determined as a defective prescription drug pack.

Therefore, preferably, the integrated drug management system according to the present invention further includes the prescription drug reinspecting module 50 to inspect only the prescription drug pack, which has been determined as a defective drug pack in the prescription drug inspecting module, again.

Figure 9:
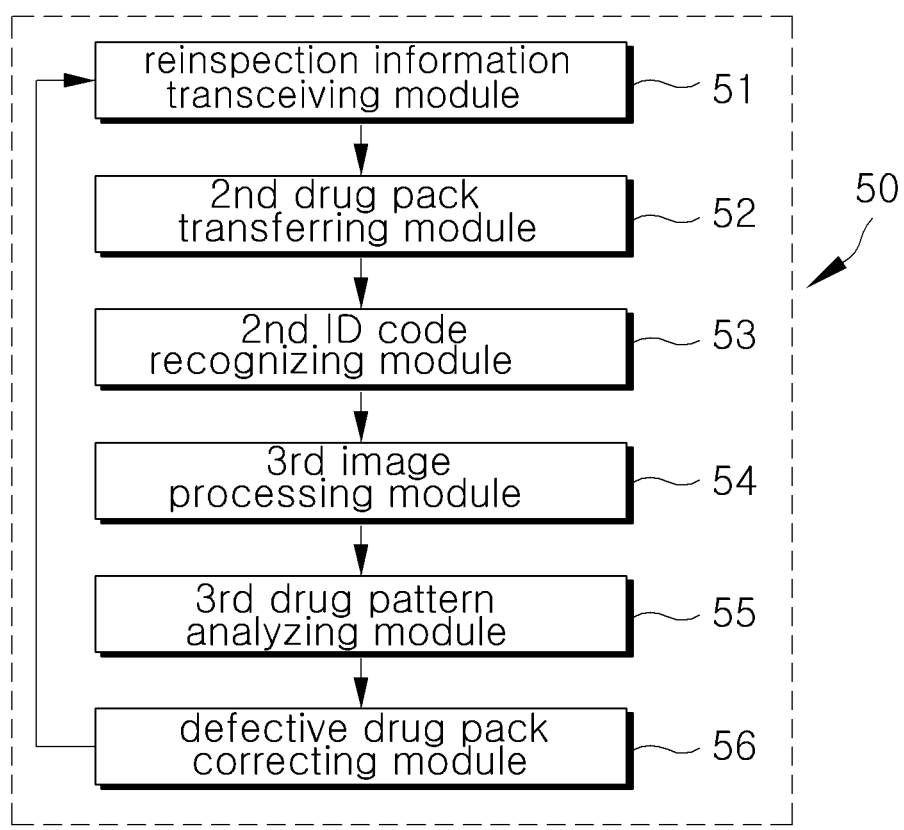
FIG. 9 is a block diagram showing the detailed structure of a prescription drug reinspecting module installed in the integrated drug management system according to the present invention.

The prescription drug reinspecting module 50 is connected to the integrated management control module 20 to reinspect the defect state of the prescription drug which has been determined as a defective drug in the prescription drug inspecting module 40. The prescription drug reinspecting module 50 according to the present invention includes a reinspection information transceiving module 51, a second drug pack transferring module 52, a second ID code recognizing module 53, a third image processing module 54, a third drug pattern analyzing module 55, and a defective drug pack correcting module 56 as shown in FIG. 9.

The reinspection information transceiving module 51 receives prescription information from the prescription information server or the hospital server 200, receives the defect information of the prescription drug pack from the prescription drug inspecting module 40, and transmits the reinspection information of the prescription drug pack.

The second drug pack transferring module 52 is connected to the reinspection information transceiving module 51 to transfer the drug pack which has been determined as a defective pack in the prescription drug making module 30. The second drug pack transferring module 52 according to the present invention preferably moves a bundle of defective drug packs at a high speed by using two winding rollers.

The drug pack determined as a defective drug pack in the prescription drug inspecting module 40 is moved by driving the second drug pack transferring module 52, so that individual drugs can be rearranged in the defective drug pack.

The second ID code recognizing module 53 is connected to the second drug pack transferring module 52 to recognize the ID code created on the prescription drug pack by the ID code creating module 34 and recognize a label of the prescription drug pack determined as a defective pack, which is created by the label creating module 46.

Figure 10:
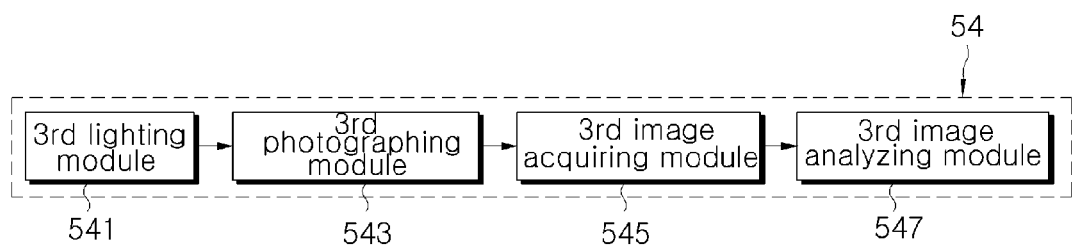
FIG. 10 is a block diagram showing the detailed structure of a third image processing module installed in the integrated drug management system according to the present invention.
Figure 11:
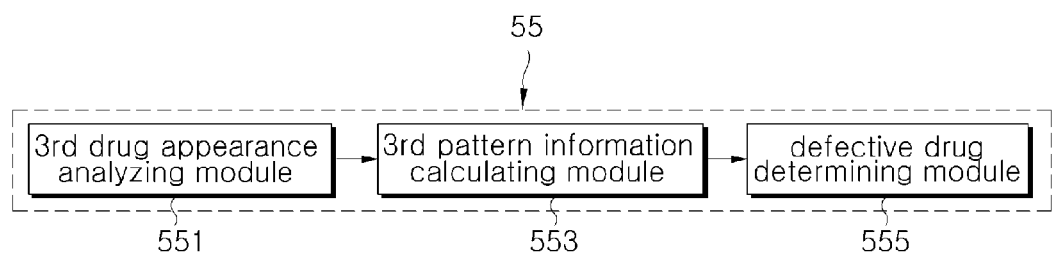
FIG. 11 is a block diagram showing the detailed structure of a third drug pattern analyzing module installed in the integrated drug management system according to the present invention.

The third image processing module 54 is connected to the second ID code recognizing module 53 to photograph the defective prescription drug pack and process the image of the photographed defective prescription drug pack. The third image processing module 54 according to the present invention includes a third lighting module 541, a third photographing module 543, a third image acquiring module 545, and a third image analyzing module 547 as shown in FIG. 10.

The third lighting module 541 illuminates the defective prescription drug pack which is arranged, and the third photographing module 543 is connected to the third lighting module 541 to photograph the defective prescription drug pack which is arranged.

Similarly to the second photographing module 443, the third photographing module 543 according to the present invention preferably acquires both of a color image and a black & white image of the defective prescription drug pack by adjusting the brightness intensity of the third lighting module 541.

The third image acquiring module 545 is connected to the third photographing module 541 to acquire the image frame of the defective prescription drug pack. The third image analyzing module 547 is connected to the third image acquiring module 545 to analyze the independent region of the individual drug contained in the image of the defective prescription drug pack.

Similarly to the second image analyzing module 447, the third image analyzing module 547 according to the present invention extracts the outer line of the independent region of the individual drug contained from the image of the defective prescription drug pack.

The third drug pattern analyzing module 55 is connected to the third image processing module 54 to analyze a drug pattern of the defective prescription drug pack so that the defect state of the prescription drug pack is determined. The third drug pattern analyzing module 55 according to the present invention includes a third drug appearance analyzing module 551, a third pattern information calculating module 553, and a defective drug determining module 555.

The third drug appearance analyzing module 551 analyzes the appearance information of an individual drug by using the independent region of the image of the individual drug contained in the image of the defective prescription drug pack. The third pattern information calculating module 553 is connected to the third drug appearance analyzing module 551 to calculate the pattern information containing the appearance graph and the shape code of the individual drug.

The defective drug determining module 555 is connected to the third pattern information calculating module 553 to determine if the pattern information of the individual drug matches with drug information contained in the prescription information, thereby determining the defect state of the individual drug.

The defective drug pack correcting module 56 is connected to the third drug pattern analyzing module 55 to correct drugs of the prescription drug pack, which has been determined as a defective pack, so that the drug information of the prescription drug pack can match with the prescription information.

Figure 12:
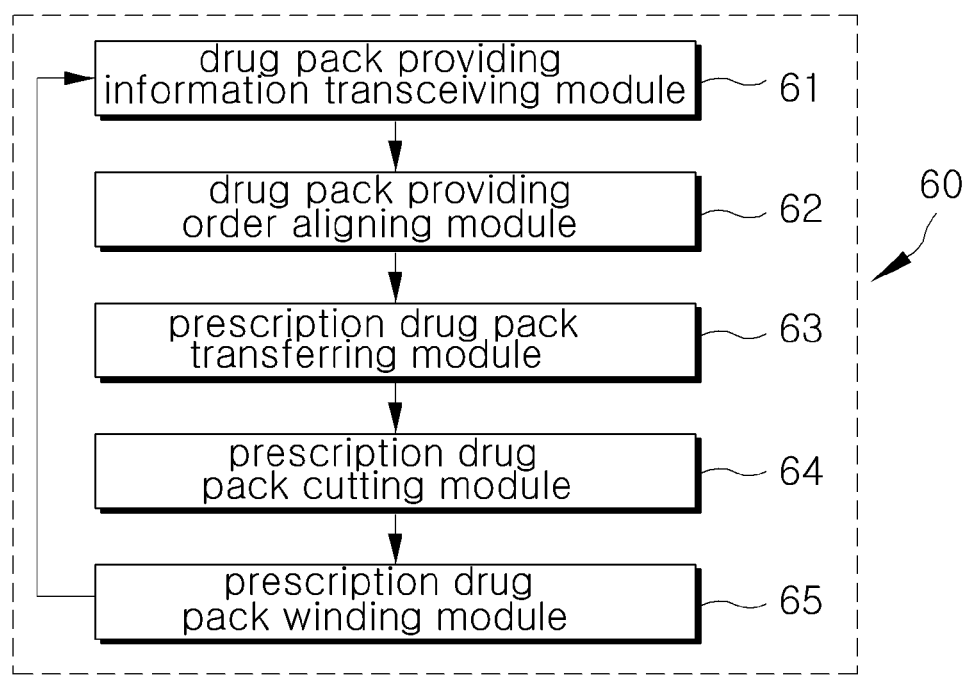
FIG. 12 is a block diagram showing the detailed structure of a drug pack providing module installed in the integrated drug management system according to the present invention.

The drug pack providing module 60 is connected to the integrated management control module 20 to provide drug packs to each ward or each patient. As shown in FIG. 12, the drug pack providing module 60 according to the present invention includes a drug pack providing information transceiving module 61, a drug pack providing order aligning module 62, a prescription drug pack transferring module 63, a prescription drug pack cutting module 64, and a prescription drug pack winding module 65.

The drug pack providing information transceiving module 61 receives the prescription information from the hospital server 200, and transmits the provision information of the prescription drug packs.

The drug pack providing order aligning module 62 is connected to the drug pack providing information transceiving module 61 to sort the order to provide prescription drug packs according to wards or patients. The prescription drug pack transferring module 63 is connected to the drug pack providing order aligning module 62 to transfer the prescription drug packs.

The prescription drug pack cutting module 64 is connected to the prescription drug pack transferring module 63 to cut the prescription drug packs, which are transferred, based on the information of each ward or each patient. The prescription drug pack winding module 65 is connected to the prescription drug pack cutting module 64 to wind and provide the cut prescription drug packs.

If the winding operation of the prescription drug pack winding module 65 is completed, the provision information of the prescription drug pack is transmitted through the drug pack providing information transceiving module 61.

The integrated information providing module 70 is connected to the integrated management control module 20 to store the information of the registration of drug management information, the preparation situation of prescription drugs, the inspection for the defect of the prescription drugs, and a manager.

Hereinafter, a method of providing a prescription drug by using the integrated drug management system according to the present invention will be described.

Figure 13:
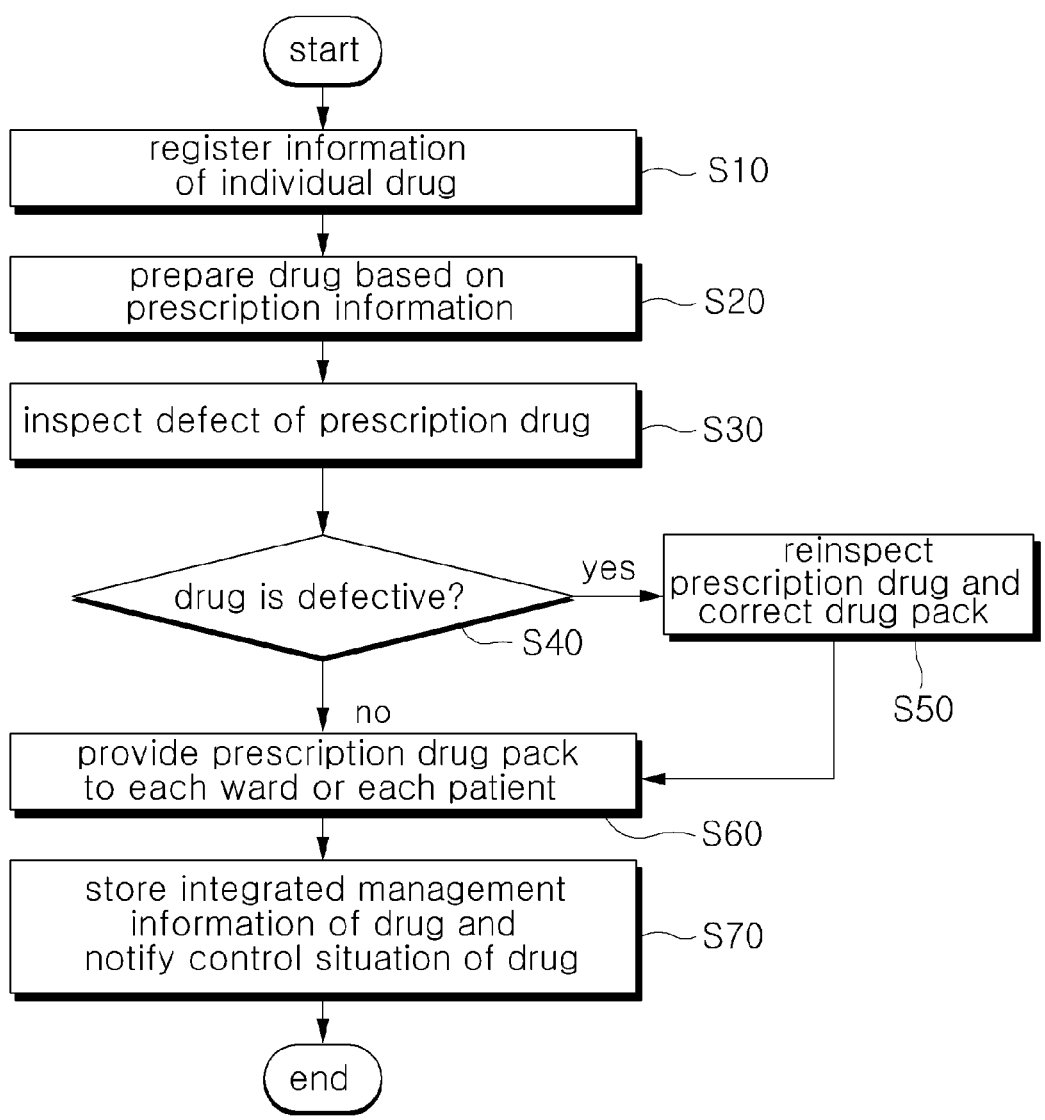
FIG. 13 is a flowchart showing a method of providing a prescription drug according to the present invention.

FIG. 13 is a flowchart showing the method of providing the prescription drug according to the present invention. First, the information of an individual drug is registered by using the drug information managing module 10 (step S10).

Figure 14:
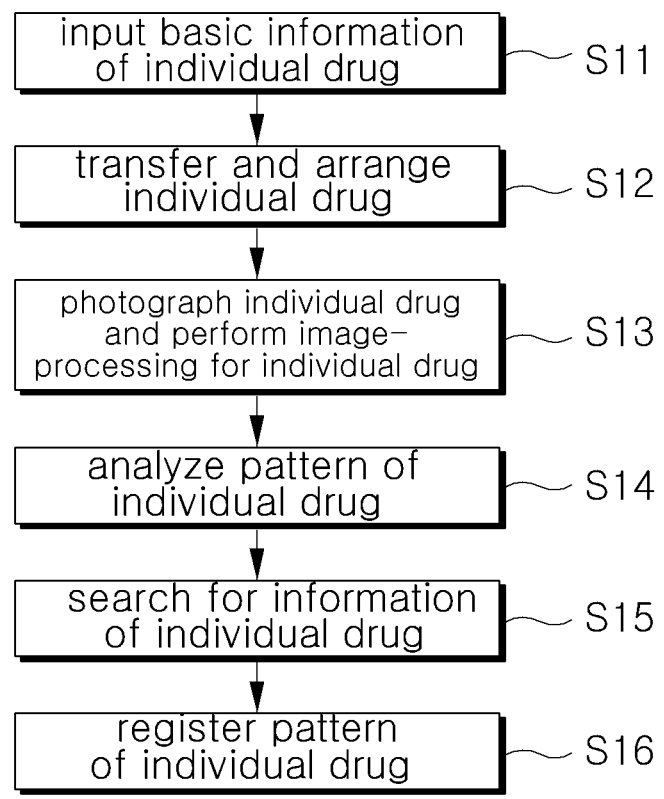
FIG. 14 is a detailed flowchart showing step S10 in the method of providing the prescription drug according to the present invention.

As shown in FIG. 14, in step S10, the basic information of the individual drug is input by using the drug information inputting module 11 (step S11)

In step S11, the basic information of the individual drug contains the name of the drug, the manufacturer of the drug, the expiration date of the drug, and the information of the manufacture date of the drug.

Next, the individual drug is transferred to the first image processing module 13 and arranged by using the drug arranging module 12 (step S12).

Subsequently, the individual drug is photographed and the image of the photographed individual drug is processed by using the first image processing module 13 (step S13).

Figure 15:
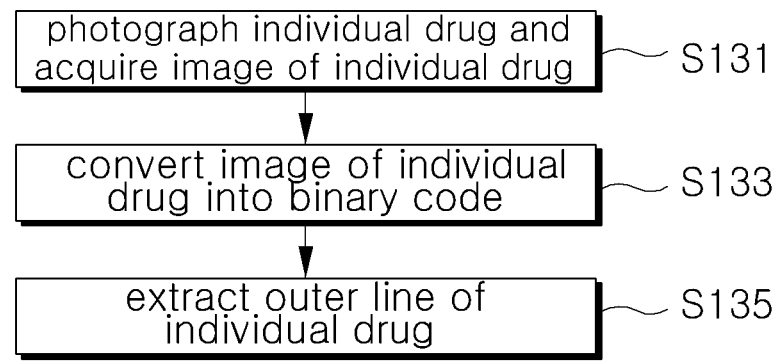
FIG. 15 is a detailed flowchart showing step S13 in the method of providing the prescription drug according to the present invention.

As shown in FIG. 15, in step S13, the individual drug is photographed at various angles by using the first photographing module 133, the image of the photographed individual drug is acquired by using the first image acquiring module 135 (step S131). Subsequently, the image of the individual drug is converted into a binary image (step S133) and the outer line of the image region of the individual drug is extracted (step S135) by using the first image analyzing module 137.

Next, the pattern of the individual drug is analyzed by using the first drug pattern analyzing module 14 (step S14).

Figure 16:
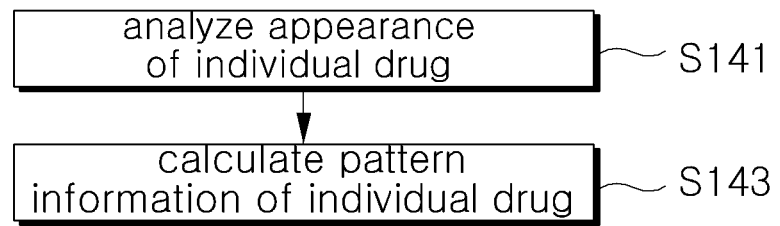
FIG. 16 is a detailed flowchart showing step S14 in the method of providing the prescription drug according to the present invention.

As shown in FIG. 16, in step S14, the appearance information of the individual drug containing the information of the color, the shape, and the size of the individual drug is analyzed by using the first drug appearance analyzing module 141 (step S141), and the pattern information of the individual drug is calculated by using the first pattern information calculating module 143 (step S143).

Subsequently, the information of the individual drug, which has been previously registered, is searched by using the drug information searching module 15 (step S15).

In this case, step S15 is to search for the previously registered information of the individual drug matching with the pattern information of the individual drug calculated in step S14.

Thereafter, the pattern information of the individual drug is stored in the pattern information storing module 16 (step S16).

Through step S16 of the present invention, the pattern information of the individual drug calculated by photographing the individual drug at various angles can be stored and managed together with the basic information of the individual drug.

Next, a drug is prepared based on prescription information by using the prescription drug making module 30 (step S20).

Figure 17:
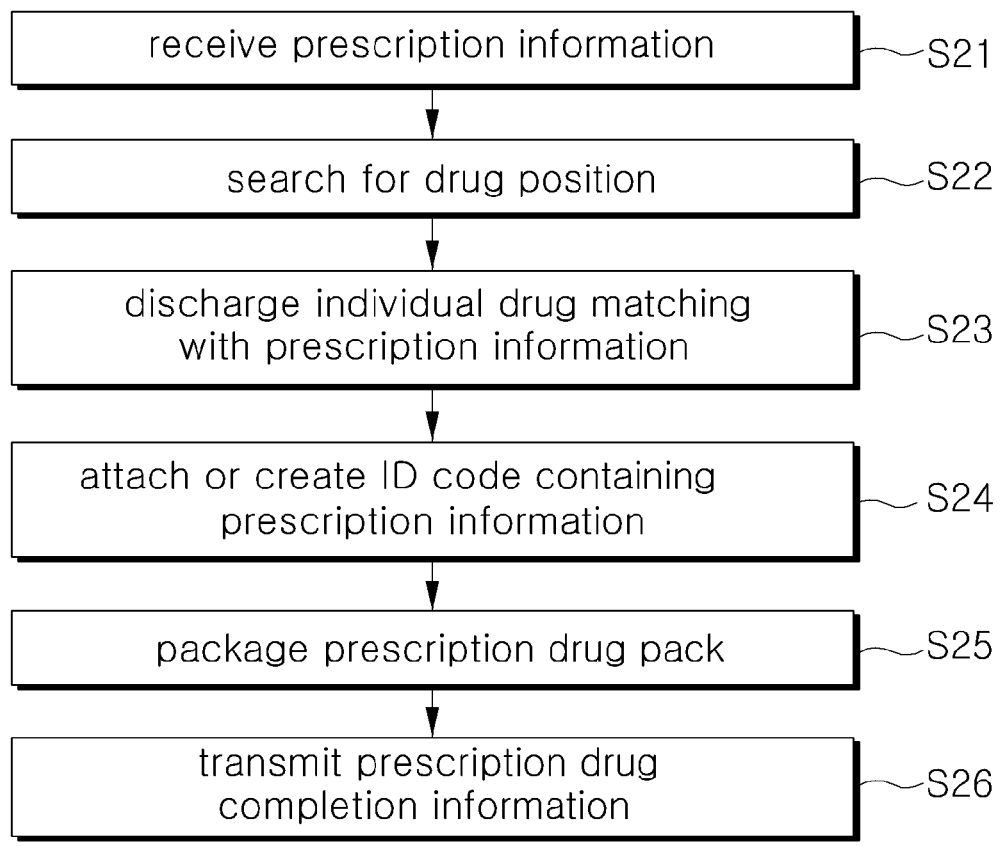
FIG. 17 is a detailed flowchart showing step S20 in the method of providing the prescription drug according to the present invention.

As shown in FIG. 17, in step S20, the prescription information transceiving module 31 receives the prescription information from the hospital server 200 (step S21), and the drug position searching module 32 searches for the position of the individual drug matching with the prescription information (step S22).

Next, the drug discharging module 33 discharges a individual drug matching with the prescription information (step S23), and the ID code creating module 34 creates an ID code containing the prescription information and attaches the ID code on the prescription drug pack (step S24).

Thereafter, the drug pack packaging module 35 inserts the discharged individual drug into a drug pack and packages the drug pack (step S25). After the prescription drug has been made, the prescription information transceiving module 31 transmits the prescription drug completion information to the hospital server 200 or the integrated management control module 20 (step S26).

Subsequently, the prescription drug inspecting module 40 inspects the defect state of the prescription drug (step S30).

Figure 18:
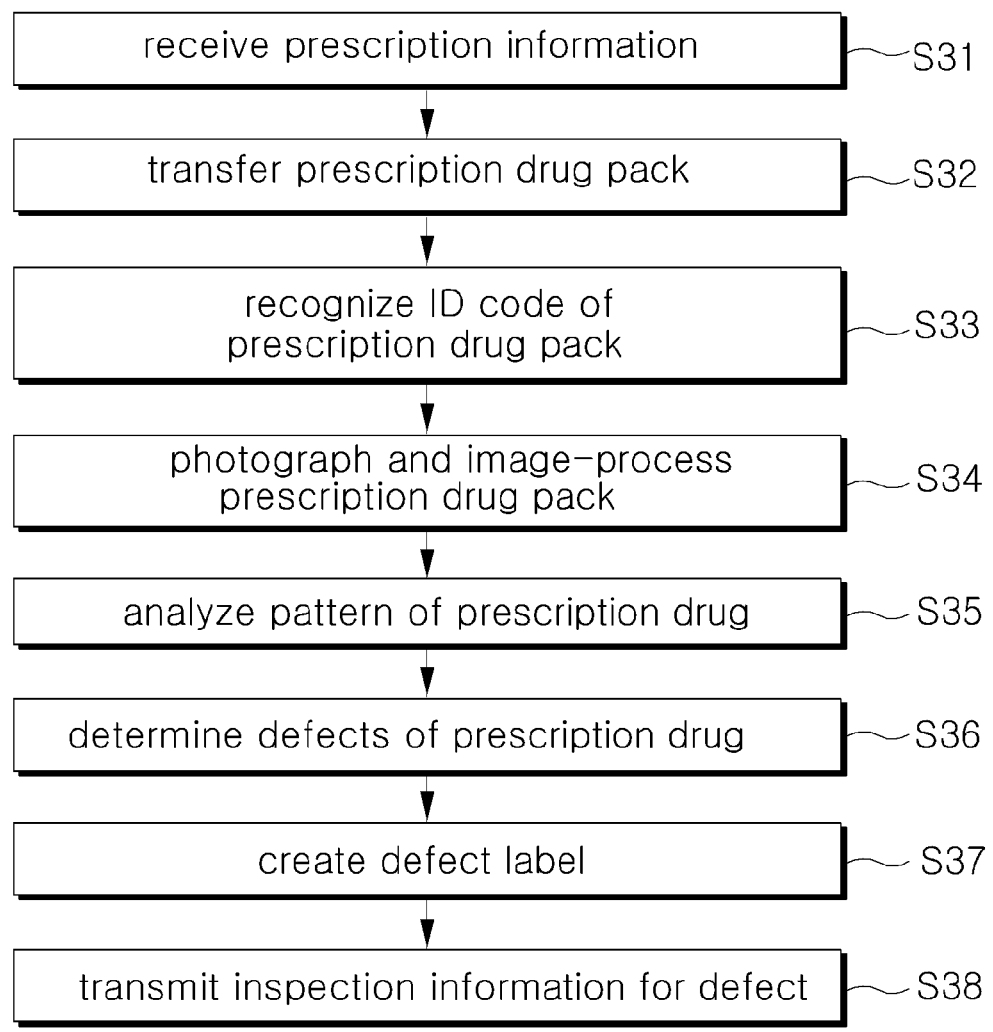
FIG. 18 is a detailed flowchart showing step S30 in the method of providing the prescription drug according to the present invention.

As shown in FIG. 18, in step S30, the inspection information transceiving module 41 receives the prescription information from the hospital server 200 (step S31), and the first drug pack transferring module 42 sequentially transfers the prescription drugs (step S32).

Next, the first ID code recognizing module 43 recognizes the ID code formed on the prescription drug pack (step S33), and the second image processing module 44 photographs the prescription drug pack and processes the image of the photographed prescription drug pack (step S34).

Figure 19:
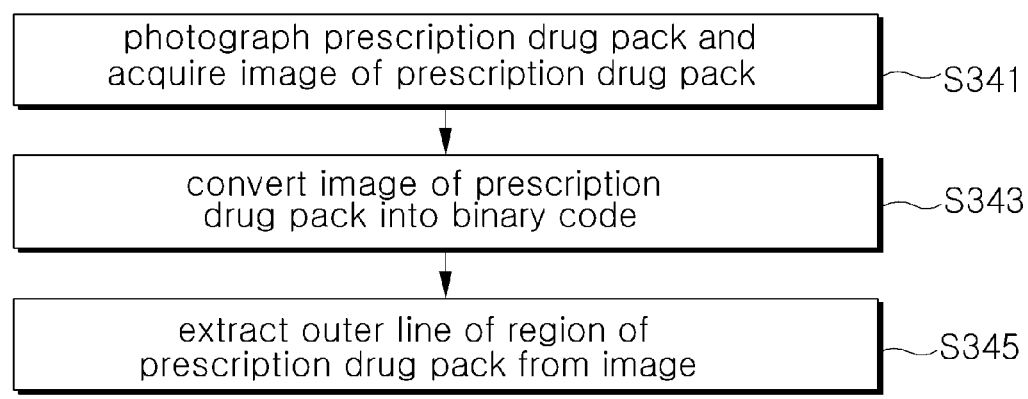
FIG. 19 is a detailed flowchart showing step S34 in the method of providing the prescription drug according to the present invention.

As shown in FIG. 19, in step S34, the second photographing module 443 photographs the prescription drug pack, and the second image acquiring module 445 acquires the image of the photographed prescription drug pack (step S341).

Thereafter, the second image analyzing module 447 converts the image of the prescription drug pack into a binary image (step S343), and the outer line of the individual drug of the prescription drug pack image is extracted (step S345).

Next, the second drug pattern analyzing module 45 analyzes the pattern information of the drug inserted into the prescription drug pack (step S35).

Figure 20:
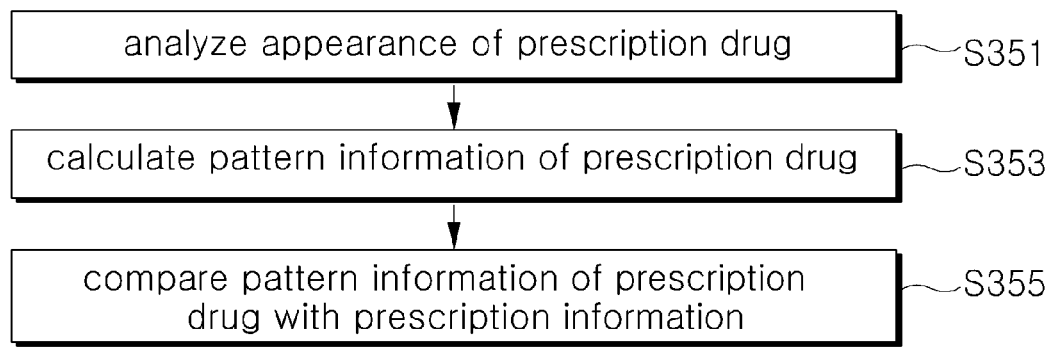
FIG. 20 is a detailed flowchart showing step S35 in the method of providing the prescription drug according to the present invention.

In step S35, as shown in FIG. 20, the second drug appearance analyzing module 451 analyzes the shape, the color, and the mark of the drug (step S351), the second pattern information calculating module 453 calculates the pattern information of the prescription drug (step S353), and the drug defect determining module 455 compares the pattern information of the prescription drug with the prescription information (step S355).

Thereafter, the drug defect determining module 455 determines the defect of the prescription drug (step S36). If the defect of the prescription drug is determined, the label creating module 46 creates the label representing the defect on the prescription drug pack or attaches the label to the prescription drug pack (step S37).

Thereafter, the inspection information transceiving module 41 transmits an inspection result to the hospital server 200 and the integrated management control module 20 after the inspection for the defect of the prescription drug pack has been completed.

Next, the integrated management control module 20 determines the defect state of the prescription drug (step S40). If the defective drug exists, the prescription drug reinspecting module 50 reinspects only the defective drug pack (step S50).

Figure 21:
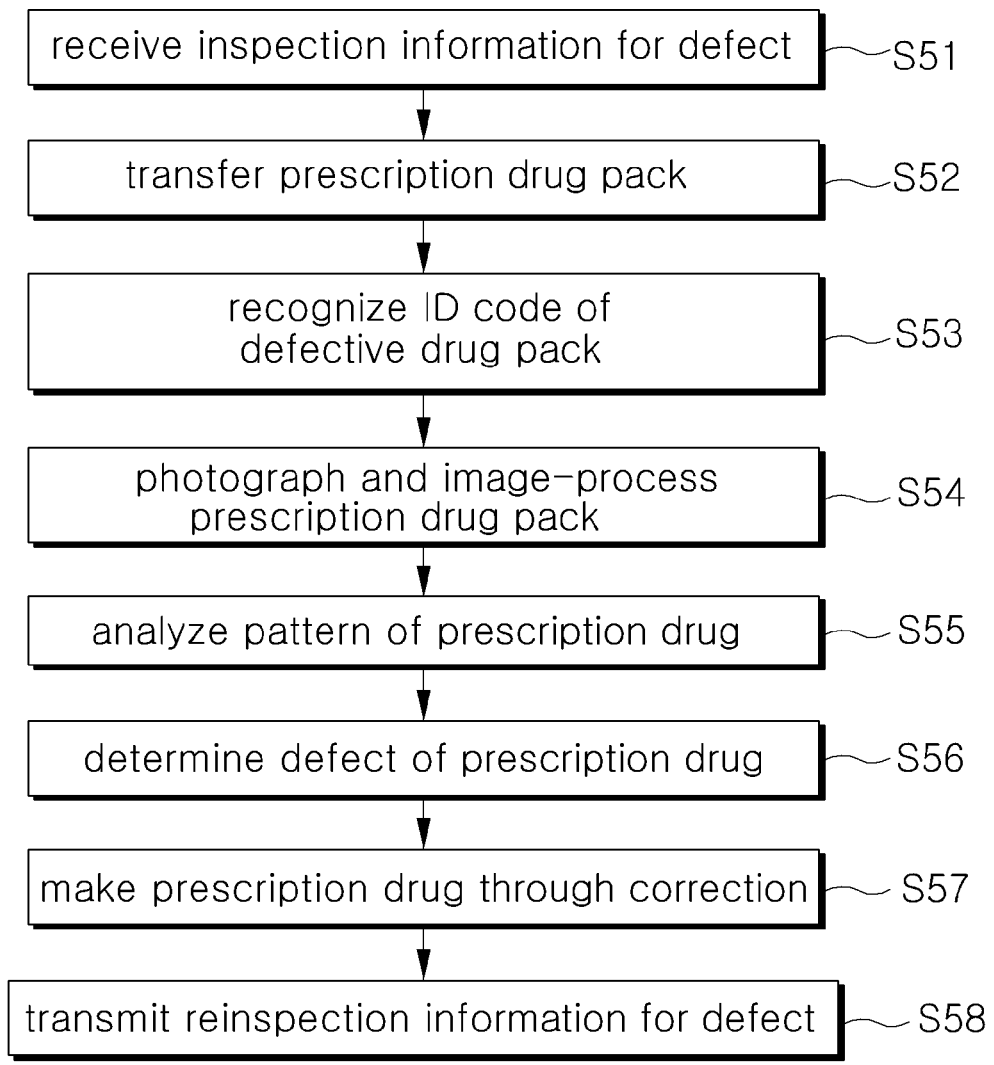
FIG. 21 is a detailed flowchart showing step S50 in the method of providing the prescription drug according to the present invention.

As shown in FIG. 21, in step S50, the reinspection information transceiving module 51 receives the information of the inspection result for the defect of the prescription drug pack of the prescription drug inspecting module 40 and receives the prescription information from the hospital server 200 (step S51).

Thereafter, the second drug pack transferring module 52 transfers the prescription drug pack determined as a defective drug pack (step S52), and the second ID code recognizing module 53 recognizes the ID code of the defective drug pack and the label representing the defect of the defective drug pack.

Subsequently, the third image processing module 54 photographs the defective drug pack and processes the image of the photographed defective drug pack (step S54).

Figure 22:
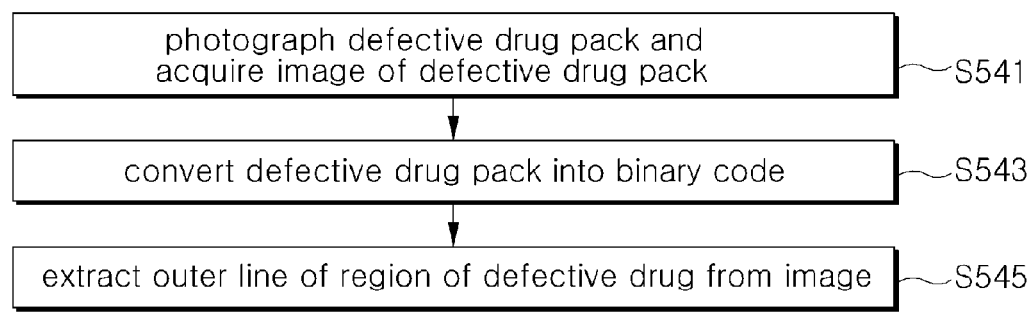
FIG. 22 is a detailed flowchart showing step S54 in the method of providing the prescription drug according to the present invention.

As shown in FIG. 22, in step S54, the third photographing module 543 photographs the defective drug pack, and the third image acquiring module 545 acquires the image of the photographed defective drug pack (step S541).

Thereafter, the third image analyzing module 547 converts the image of the defective drug pack into a binary image (step S543), and extracts the outer line of the defective drug region contained in the image.

Next, the third drug pattern analyzing module 55 determines the defect state of the defective drug (step S55).

Figure 23:
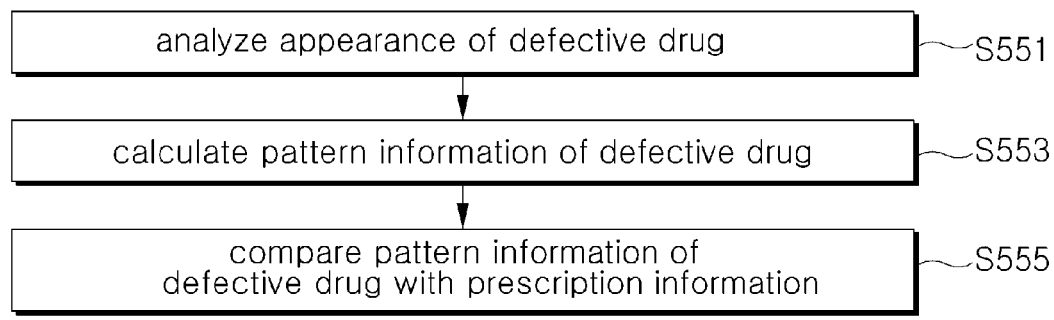
FIG. 23 is a detailed flowchart showing step S55 in the method of providing the prescription drug according to the present invention.

As shown in FIG. 23, in step S55, the third drug appearance analyzing module 551 analyzes the appearance of the defective drug including the color, the shape, and the size of the defective drug (step S551), and the third pattern information calculating module 553 calculates the pattern information of the defective drug (step 553).

Thereafter, the defective drug determining module 555 compares the prescription information with the pattern information of the defective drug (step S555).

If the pattern information of the defective drug matches with the prescription information in step S555 so that the prescription drug is not defective, a step of correcting the label representing the drug defect is additionally performed preferably. If the pattern information of the defective drug does not match with the prescription information in step S555 so that the prescription drug is determined as a defective drug (step S56), the defective drug pack correcting module 56 correctly make the prescription drug (step S57).

Thereafter, the reinspection information transceiving module 51 transmits the information according to the reinspection completion of the prescription drug pack to the integrated management control module 20 to store the reinspection information (step S58).

According to the method of providing the prescription drug of the present invention, after step S58 has been performed, the prescription drug making module 30 may make prescription drug according to the control signal of the integrated management control module 20.

Therefore, if the defect of the prescription drug is determined, the defective drug pack correcting module 56 or the prescription drug making module 30 may make a prescription drug again.

Thereafter, the drug pack providing module 60 provides prescription drug packs according to the wards or the patients (step S60).

Figure 24:
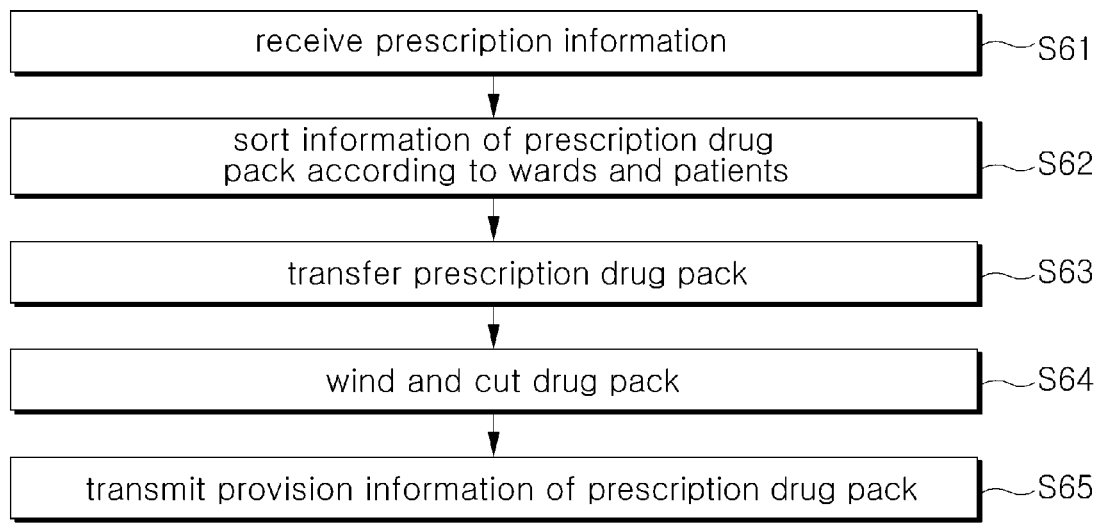
FIG. 24 is a detailed flowchart showing step S60 in the method of providing the prescription drug according to the present invention.

As shown in FIG. 24, in step S60, the drug pack providing information transceiving module 61 receives the prescription information from the hospital server 200 (step S61), and the drug pack providing order aligning module 62 sorts information of prescription drug packs according to wards or patients (step S62).

Next, the prescription drug pack transferring module 63 transfers the prescription drug pack which has been subject to the defect inspection (step S63), the prescription drug pack cutting module 64 cuts prescription drug packs according to wards or patients, and the prescription drug pack winding module 65 winds the cut prescription drug packs (step S64).

Subsequently, the drug pack providing information transceiving module 61 transmits the information to provide the drug packs to the hospital server 200 (step S64).

As described above, when applying the method of providing prescription drugs according to the present invention, a prescription drug determined as a defective drug based on the pattern information of an individual drug, which is previously registered, is corrected, so that the prescription drug exactly matching with the prescription information can be provided.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An integrated drug management system comprising:
a computer processor;
a drug information managing module comprising a first image processing module to manage a basic information and a pattern information of an individual drug, wherein the first image processing module photographs the individual drug and analyzes an image of the individual drug;
an integrated management control module connected to the drug information managing module to control a drug management work and a prescription drug management work;
a prescription drug making module connected to the integrated management control module to provide a prescription drug pack having a plurality of individual drugs according to a prescription information;
a prescription drug inspecting module comprising a second image processing module and connected to the integrated management control module to inspect a defect state of the prescription drug pack, wherein the second image processing module photographs the prescription drug pack and analyzes an outer line of the individual drug contained in the image of the prescription drug pack;
a prescription drug reinspecting module comprising a third image processing module and connected to the integrated management control module to reinspect the defect state of the prescription drug pack which has been determined as a defective prescription drug pack, wherein the third image processing module photographs the defective prescription drug pack and analyzes an outer line of the individual drug contained in the image of the photographed defective prescription drug pack; and a drug pack providing module connected to the integrated management control module to provide the prescription drug pack to each ward or each patient.

2. The integrated drug management system of claim 1, wherein the drug information managing module comprises:

a drug information inputting module to input the basic information of the individual drug to be registered;

a drug arranging module connected to the drug information inputting module to arrange the individual drug;

the first image processing module connected to the drug arranging module to process the image of the individual drug after photographing the individual drug; a first drug pattern analyzing module connected to the first image processing module to analyze a pattern of the individual drug by analyzing the image of the individual drug; a drug information searching module connected to the first drug pattern analyzing module to search for a drug information which has been previously registered; and a pattern information storing module connected to the drug information searching module to store the basic information and the pattern information of the individual drug.

3. The integrated drug management system of claim 2, wherein the first image processing module comprises:

a first lighting module to illuminate the individual drug that has been placed; a first photographing module connected to the first lighting module to photograph the individual drug that has been arranged;

a first image acquiring module connected to the first photographing module to acquire the image frame of the individual drug; and a first image analyzing module connected to the first image acquiring module to analyze an independent region of the image of the individual drug.

4. The integrated drug management system of claim 3, wherein the first drug pattern analyzing module comprises:

a first drug appearance analyzing module to analyze an appearance information of the individual drug by using the independent region of the individual drug image; and a first pattern information calculating module connected to the first drug appearance analyzing module to calculate the pattern information including an appearance graph and a shape code of the individual drug, wherein the appearance graph of the individual drug is calculated based on a distance from the center to the outer line of the individual drug, and wherein the shape code of the individual drug is calculated by classifying shape types according to the shape of the outer line of the photographed individual drug.

5. The integrated drug management system of claim 1, wherein the prescription drug making module comprises:

a prescription information transceiving module to transmit/receive the prescription information to/from a prescription information server or a hospital server;

a drug position searching module connected to the prescription information transceiving module to search for a storage position of the drug corresponding to the prescription information;

a drug discharging module connected to the drug position searching module to discharge the individual drug matching with the prescription information;

an ID code creating module connected to the drug discharging module to create an ID code including a prescription drug information of the prescription drug pack and a patient information, and attach the ID code to the prescription drug pack or form the ID code on the prescription drug pack; and a drug pack packaging module connected to the ID code creating module to insert the discharged prescription drug into the prescription drug pack and to package the prescription drug pack.

6. The integrated drug management system of claim 5, wherein the prescription drug inspecting module comprises:

an inspection information transceiving module to receive the prescription information from the prescription information server or the hospital server to transmit an inspection result of the prescription drug pack;

a first drug pack transferring module connected to the inspection information transceiving module to sequentially transfer the drug prescription pack, wherein the first drug pack transferring module includes a transfer belt to sequentially transfer a bundle of prescription drug packs on the transfer belt;

a first ID code recognizing module connected to the first drug pack transferring module to recognize an ID member created by the ID code creating module;

the second image processing module connected to the first ID code recognizing module to individually photograph the prescription drug pack to process a prescription drug pack image;

a second drug pattern analyzing module connected to the second image processing module to analyze the prescription drug pack image, to analyze a pattern of the prescription drug, and to determine the defect state of the prescription drug; and a label creating module connected to the second drug pattern analyzing module to create a label representing a defect state of the prescription drug pack so that the label is attached to the prescription drug pack.

7. The integrated drug management system of claim 6, wherein the second image processing module comprises:

a second lighting module to illuminate the individual prescription drug pack that has been arranged;

a second photographing module connected to the second lighting module to photograph the individual prescription drug pack that has been arranged;

a second image acquiring module connected to the second photographing module to acquire an image frame of the individual prescription drug pack image that has been placed; and a second image analyzing module connected to the second image acquiring module to analyze an independent region of the individual drug contained in the individual drug pack image, wherein the second photographing module acquires both of a color image and a black and white image of the prescription drug pack by adjusting the brightness of the second lighting module.

8. The integrated drug management system of claim 7, wherein the second drug pattern analyzing module comprises:

a second drug appearance analyzing module to analyze an appearance information of the individual drug by using the independent region of an individual drug image contained in the individual drug pack image;

a second pattern information calculating module connected to the second drug appearance analyzing module to calculate the pattern information including an appearance graph and a shape code of the individual drug; and a drug defect determining module to determine a drug defect state by determining if the pattern information of the individual drug matches with the drug information contained in the prescription information.

9. The integrated drug management system of claim 1, wherein the prescription drug reinspecting module comprises:
a reinspection information transceiving module to receive the prescription information from a prescription information server or a hospital server, to receive a defect information of the prescription drug pack from the prescription drug inspecting module, and to transmit a reinspection information of the prescription drug pack;
a second drug pack transferring module connected to the reinspection information transceiving module to transfer a drug pack which has been determined as a defective drug pack in the prescription drug making module, wherein the second drug pack transferring module moves the defective drug pack by two winding rollers so that individual drugs in the defective drug pack can be rearranged;
a second ID code recognizing module connected to the second drug pack transferring module to recognize an ID code of the prescription drug pack determined as the defective drug pack;
a third image processing module connected to the second ID code recognizing module to photograph the defective prescription drug pack and process the image of the defective prescription drug pack;
a third drug pattern analyzing module connected to the third image processing module to analyze a drug pattern of the defective prescription drug pack so that a defect state of the prescription drug pack is determined; and
a defective drug pack correcting module connected to the third drug pattern analyzing module to correct drugs of the prescription drug pack, which has been determined as the defective drug pack, so that a drug information of the prescription drug pack matches with the prescription information.

10. The integrated drug management system of claim 9, wherein the third image processing module comprises:
a third lighting module to illuminate the defective prescription drug pack which has been arranged; a third photographing module connected to the third lighting module to photograph the defective prescription drug pack which has been arranged;
a third image acquiring module connected to the third photographing module to acquire an image of the defective prescription drug pack; and
a third image analyzing module connected to the third image acquiring module to analyze an independent region of the individual drug contained in the defective prescription drug pack image.

11. The integrated drug management system of claim 10, wherein the third drug pattern analyzing module comprises:
a third drug appearance analyzing module to analyze an appearance information of the individual drug by using the independent region of the individual drug contained in the defective prescription drug pack image;
a third pattern information calculating module connected to the third drug appearance analyzing module to calculate the pattern information including an appearance graph and a shape code of the individual drug; and
a defective drug determining module to determine a defect state of the individual drug by determining if the pattern information of the individual drug matches with the drug information contained in the prescription information.

12. The integrated drug management system of claim 1, wherein the drug pack providing module comprises:

a drug pack providing information transceiving module to receive the prescription information and transmit a provision information of the prescription drug pack;
a drug pack providing order aligning module connected to the drug pack providing information transceiving module to sort an order to provide the prescription drug pack according to wards or patients;
a prescription drug pack transferring module connected to the drug pack providing order aligning module to transfer the prescription drug pack;
a prescription drug pack cutting module connected to the prescription drug pack transferring module to cut the prescription drug pack, which is transferred, based on an information of each ward or each patient; and
a prescription drug pack winding module connected to the prescription drug pack cutting module to wind and provide the cut prescription drug pack.

13. A method of providing a prescription drug, the method comprising:
registering a pattern information of an individual drug by a first image processing module of a drug information managing module;
preparing a drug based on a prescription information received from a hospital server by using a prescription drug making module;
inspecting a defect state of the prescription drug pack by a second image processing module of using a prescription drug inspecting module, wherein the second image processing module photographs the prescription drug pack and analyzes an outer line of the individual drug contained in the image of the prescription drug pack; and
correcting the prescription drug determined as a defective drug by a third image processing module of a defective drug pack correcting module or a prescription drug making module, wherein the third image processing module photographs the defective prescription drug pack and analyzes an outer line of the individual drug contained in the image of the photographed defective prescription drug pack.

14. The method of claim 13, wherein the registering of the pattern information of the individual drug comprises:
inputting a basic information of the individual drug by using a drug information inputting module;
transferring and arranging the individual drug by using a drug arranging module;
photographing the individual drug and processing an image of the photographed individual drug by using the first image processing module;
analyzing a pattern of the individual drug by using a first drug pattern analyzing module;
searching an information of the individual drug, which has been previously registered, by using a drug information searching module; and
storing the pattern information of the individual drug in a pattern information storing module.

15. The method of claim 14, wherein the photographing of the individual drug to process the image of the photographed individual drug comprises:
photographing the individual drug at various angles by using a first photographing module;
acquiring the image of the photographed individual drug by using a first image acquiring module; and
converting the image of the individual drug into a binary image and extracting an outer line of an individual drug region by using a first image analyzing module.

16. The method of claim 14, wherein the analyzing of the pattern of the individual drug comprises:
- analyzing an appearance of the individual drug including a color, a shape, and a size of the individual drug by using a first drug appearance analyzing module; and
- calculating the pattern information of the individual drug by using a first pattern information calculating module.

17. The method of claim 13, wherein the preparing of a drug based on the prescription information comprises:
- receiving the prescription information from the hospital server by using a prescription information transceiving module;
- searching for a position of the individual drug matching with the prescription information by using a drug position searching module;
- discharging the individual drug matching with the prescription information by using a drug discharging module;
- creating an ID code including the prescription information and attaching the ID code on the prescription drug pack by using an ID code creating module;
- enclosing the discharged individual drug into the prescription drug pack and packaging the drug pack by using a drug pack packaging module; and
- transmitting a prescription drug preparation completion information to an integrated management control module by using a prescription information transceiving module.

18. The method of claim 13, wherein the inspecting of the defect state of the prescription drug comprises:
- receiving the prescription information from the hospital server by using an inspection information transceiving module;
- transferring the prescription drug by using a first drug pack transferring module including a transfer belt;
- recognizes an ID code of the prescription drug pack by using a first ID code recognizing module;
- photographing the prescription drug pack and processing an image of the photographed prescription drug pack by using the second image processing module;
- analyzing a pattern information of the prescription drug by using a second drug pattern analyzing module; and
- determining determines the defect state of the prescription drug by using the second drug pattern analyzing module.

19. The method of claim 18, wherein the photographing of the prescription drug pack to process the image of the photographed prescription drug pack comprises:
- photographing the prescription drug pack by using a second photographing module;
- acquiring the image of the photographed prescription drug pack by using a second image acquiring module; and
- converting the image of the prescription drug pack into a binary image, and extracting an outer line of a prescription drug region by using a second image analyzing module.

20. The method of claim 18, wherein the analyzing of the pattern information of the prescription drug comprises:
- analyzing a drug appearance including a color, a shape, and a size of the prescription drug by using a second drug appearance analyzing module;
- calculating the pattern information of the prescription drug by using a second pattern information calculating module; and
- determining the defect state of the prescription drug by comparing the pattern information of the prescription drug with the prescription information by using a drug defect determining module.

21. The method of claim 18, further comprising:
- creating a defect label when a defect of the prescription drug is determined to attach the defect label to the prescription drug pack by using a label creating module; and
- transmitting an inspection information of the defect of the prescription drug by an inspection information transceiving module, after determining the defect state of the prescription drug.

22. The method of claim 13, further comprising:
- receiving a drug pack defect inspecting information by using a reinspection information transceiving module;
- transferring a defective drug pack by using a second drug pack transferring module;
- recognizing an ID code of the defective drug pack by using a second ID code recognizing module; photographing the defective drug pack to process an image of the photographed defective drug pack by using a third image processing module;
- analyzing a pattern of a defective drug by using a third drug pattern analyzing module; and determining the defect state of the prescription drug by using the third drug pattern analyzing module, after inspecting the defect of the prescription drug.

23. The method of claim 22, wherein the photographing of the defective drug pack to process the image of the photographed defective drug pack comprises:
- photographing the defective drug pack by using a third photographing module;
- acquiring the image of the photographed defective drug pack by using a third image acquiring module; and
- converting the image of the defective drug pack into a binary image and extracting an outer line of a defective drug region by using a third image analyzing module.

24. The method of claim 22, wherein the analyzing of the pattern of the defective drug comprises:
- analyzing a drug appearance including a color, a shape, and a size of the defective drug by using a third drug appearance analyzing module;
- calculating a pattern information of the defective drug by using a third pattern information calculating module; and
- determining the defect state of the prescription drug by comparing the prescription information with the pattern information of the defective drug by using a defective drug determining module.

25. The method of claim 13, further comprising:
- receiving the prescription information from the hospital server by using a drug pack providing information transceiving module;
- sorting a prescription drug pack information according to wards or patients by using a drug pack providing order aligning module;
- transferring the prescription drug pack which has been subject to defect inspection by using a prescription drug pack transferring module;
- cutting the prescription drug pack according to wards or patients by using a prescription drug pack cutting module;
- winding the cut prescription drug pack by using a prescription drug pack winding module; and
- transmitting a drug pack providing information to the hospital server by using a drug pack providing information transceiving module, after correcting the prescription drug determined as the defective drug.

* * * * *